(12) United States Patent
Hedberg et al.

(10) Patent No.: US 9,370,643 B2
(45) Date of Patent: Jun. 21, 2016

(54) HIGH STRENGTH BALLOON COVER

(75) Inventors: Brandon C. Hedberg, Flagstaff, AZ (US); Thomas P. Nilson, Anthem, AZ (US)

(73) Assignee: W.L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/529,896

(22) Filed: Jun. 21, 2012

(65) Prior Publication Data

US 2012/0330232 A1  Dec. 27, 2012

Related U.S. Application Data

(60) Provisional application No. 61/500,555, filed on Jun. 23, 2011.

(51) Int. Cl.
*A61M 25/10* (2013.01)

(52) U.S. Cl.
CPC ............. *A61M 25/10* (2013.01); *A61M 25/104* (2013.01); *A61M 2025/1031* (2013.01); *A61M 2025/1075* (2013.01); *A61M 2025/1081* (2013.01)

(58) Field of Classification Search
CPC .............. A61M 25/10; A61M 25/104; A61M 2025/1031; A61M 2025/1075; A61M 2025/1081
USPC .................. 604/101.02, 103, 103.04–103.06, 604/103.08, 103.09, 103.11–103.14; 606/192, 194
See application file for complete search history.

(56) References Cited

U.S. PATENT DOCUMENTS

| | | | |
|---|---|---|---|
| 4,738,666 A | 4/1988 | Fuqua | |
| 5,104,376 A | 4/1992 | Crittenden | |
| 5,116,318 A | 5/1992 | Hillstead | |
| 5,137,512 A | 8/1992 | Burns et al. | |
| 5,324,261 A | 6/1994 | Amundson et al. | |
| 5,348,538 A | 9/1994 | Wang et al. | |
| 5,358,486 A * | 10/1994 | Saab .................. | A61L 29/06 604/103.06 |
| 5,358,487 A | 10/1994 | Miller | |
| 5,443,495 A | 8/1995 | Buscemi et al. | |
| 5,458,615 A | 10/1995 | Klemm et al. | |
| 5,507,768 A | 4/1996 | Lau et al. | |
| 5,545,209 A | 8/1996 | Roberts et al. | |
| 5,843,027 A | 12/1998 | Stone et al. | |
| 5,868,704 A * | 2/1999 | Campbell ............ | A61F 2/958 604/103.11 |
| 5,873,880 A | 2/1999 | Williams et al. | |
| 5,964,730 A | 10/1999 | Williams et al. | |

(Continued)

FOREIGN PATENT DOCUMENTS

| | | |
|---|---|---|
| JP | 8033720 | 2/1996 |
| WO | 2008/021025 | 2/2008 |

(Continued)

OTHER PUBLICATIONS

Definition of Adhere by dictionary.com; retrieved from http://dictionary.reference.com/browse/adhere on Apr. 30, 2015.*

(Continued)

*Primary Examiner* — Andrew Gilbert
(74) *Attorney, Agent, or Firm* — Kilpatrick Townsend & Stockton LLP

(57) ABSTRACT

A balloon cover is provided to enhance the performance of a medical balloon, the cover, in accordance with an embodiment, having overlapping portions and opposed apertures located at apexes of tapered ends of the balloon cover. A method of making balloon covers is also disclosed.

16 Claims, 15 Drawing Sheets

(56) References Cited

U.S. PATENT DOCUMENTS

| | | | |
|---|---|---|---|
| 6,537,247 B2 | 3/2003 | Shannon | |
| 6,656,213 B2 | 12/2003 | Solem | |
| 6,695,863 B1 | 2/2004 | Ramzipoor et al. | |
| 6,746,425 B1 | 6/2004 | Beckham | |
| 6,749,584 B2 | 6/2004 | Briggs et al. | |
| 6,756,094 B1 * | 6/2004 | Wang | A61L 29/041 264/512 |
| 6,923,827 B2 * | 8/2005 | Campbell | A61F 2/958 604/103 |
| 6,955,658 B2 | 10/2005 | Murray, III | |
| 7,108,684 B2 | 9/2006 | Farnan | |
| 7,195,638 B1 * | 3/2007 | Sridharan | A61M 25/104 606/194 |
| 7,641,844 B2 | 1/2010 | Melsheimer | |
| 8,016,752 B2 * | 9/2011 | Armstrong | A61M 25/0043 600/156 |
| 8,460,240 B2 * | 6/2013 | Towler | A61L 29/126 604/103.07 |
| 2003/0093086 A1 | 5/2003 | Briggs et al. | |
| 2003/0211258 A1 * | 11/2003 | Sridharan | B29C 66/73711 428/35.2 |
| 2005/0124969 A1 | 6/2005 | Fitzgerald et al. | |
| 2007/0083216 A1 | 4/2007 | Belef et al. | |
| 2007/0213759 A1 * | 9/2007 | Osborne | A61F 2/95 606/192 |
| 2007/0232996 A1 | 10/2007 | Andersen | |
| 2008/0033477 A1 | 2/2008 | Campbell et al. | |
| 2008/0097301 A1 * | 4/2008 | Alpini | A61M 25/1029 604/103.07 |
| 2008/0103444 A1 | 5/2008 | Jimenez | |
| 2008/0140173 A1 | 6/2008 | Eskaros et al. | |
| 2008/0319388 A1 | 12/2008 | Slattery et al. | |
| 2009/0043254 A1 * | 2/2009 | Pepper | A61M 25/10 604/103.07 |
| 2009/0076449 A1 | 3/2009 | Geis et al. | |
| 2009/0112159 A1 | 4/2009 | Slattery et al. | |
| 2009/0227948 A1 * | 9/2009 | Chen et al. | 604/103.02 |
| 2009/0299327 A1 * | 12/2009 | Tilson et al. | 604/500 |
| 2010/0010303 A1 | 1/2010 | Bakos | |
| 2010/0057001 A1 | 3/2010 | Chen et al. | |
| 2010/0228333 A1 | 9/2010 | Drasler et al. | |
| 2010/0318029 A1 | 12/2010 | Pepper et al. | |
| 2011/0144583 A1 | 6/2011 | Matov et al. | |
| 2013/0253466 A1 * | 9/2013 | Campbell | A61M 25/10 604/500 |

FOREIGN PATENT DOCUMENTS

| | | |
|---|---|---|
| WO | 2008/096365 | 8/2008 |
| WO | 2009/149108 | 12/2009 |
| WO | 2010/144483 | 12/2010 |

OTHER PUBLICATIONS

International Search Report and Written Opinion for PCT/US2012/055666 mailed May 2, 2013, corresponding to U.S. Appl. No. 13/619,806.

* cited by examiner

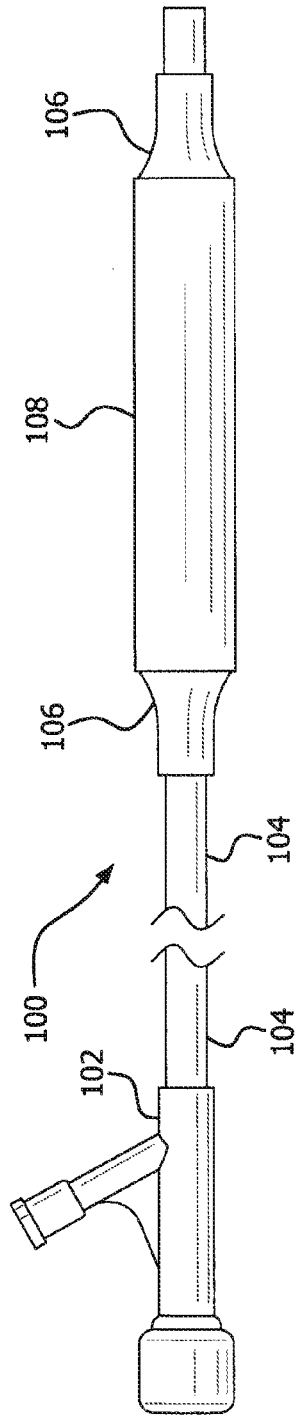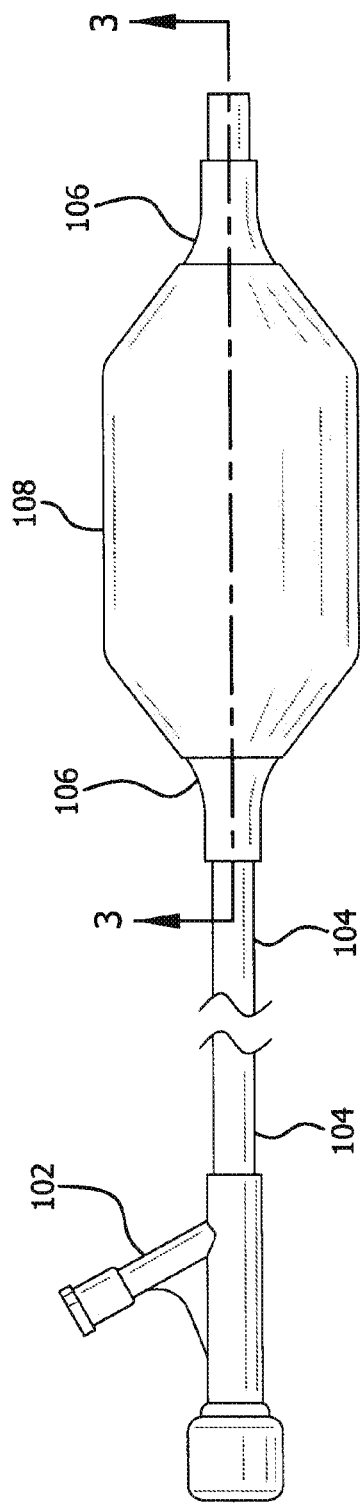
FIG. 1A
FIG. 1B

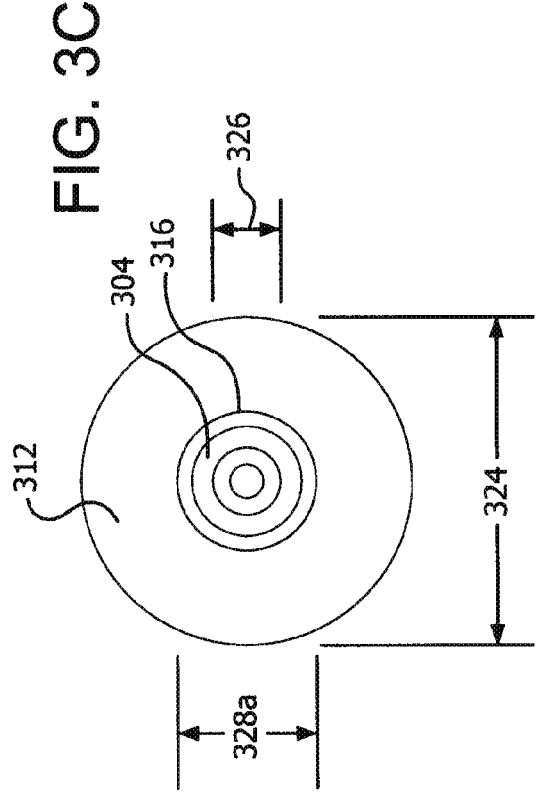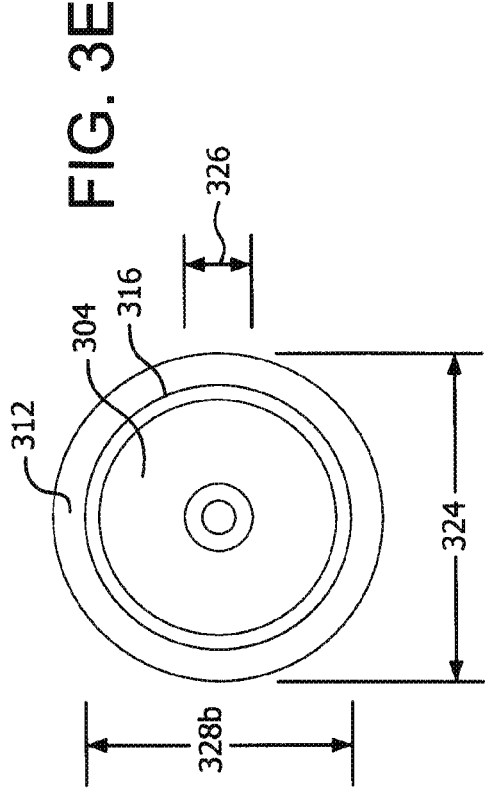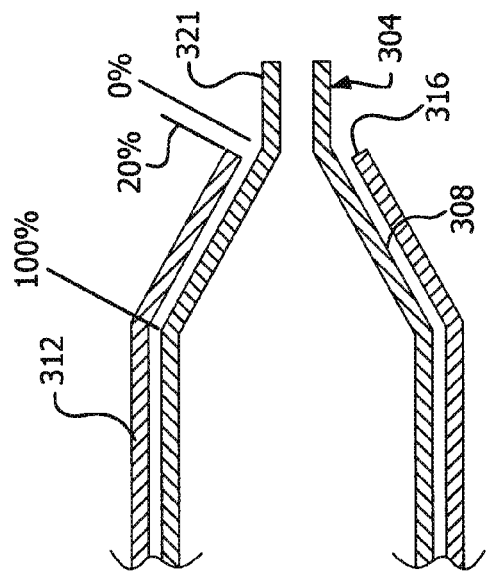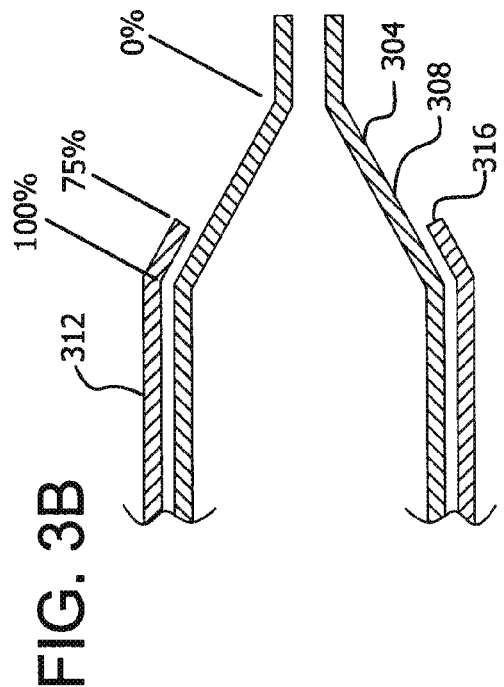

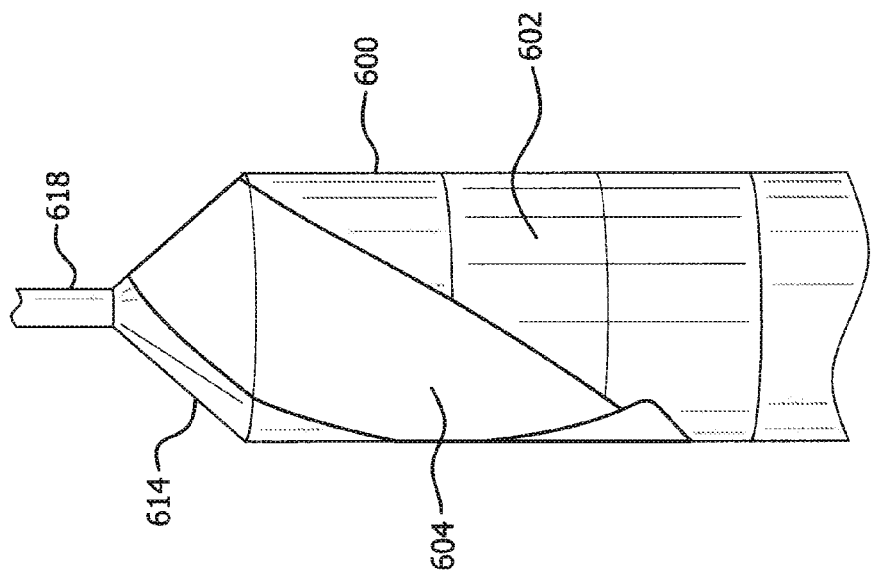
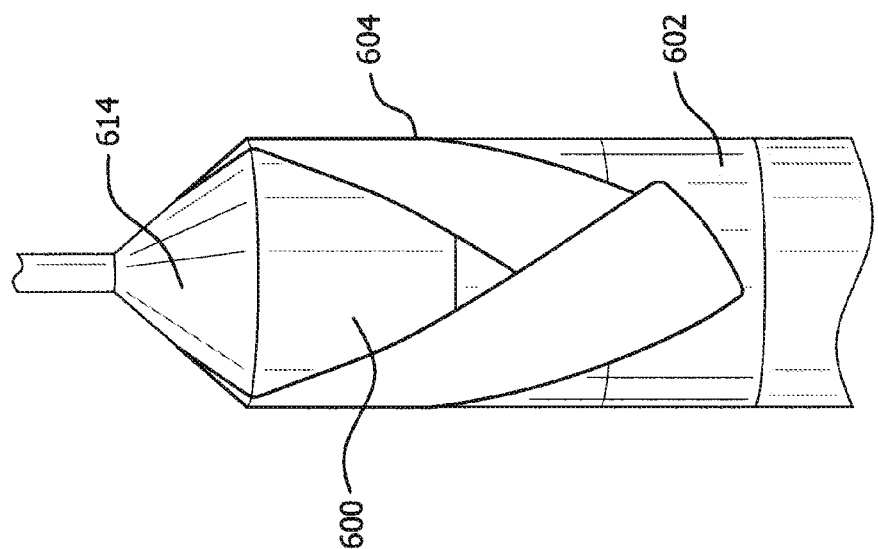

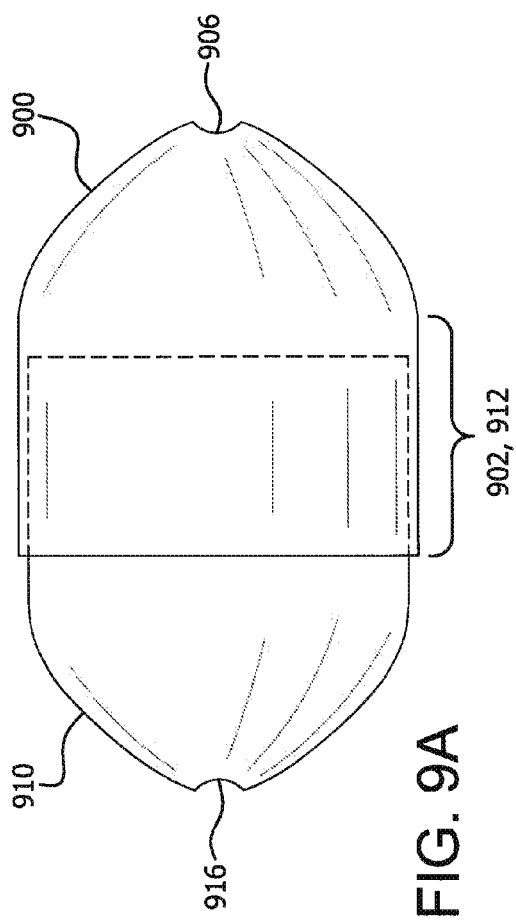
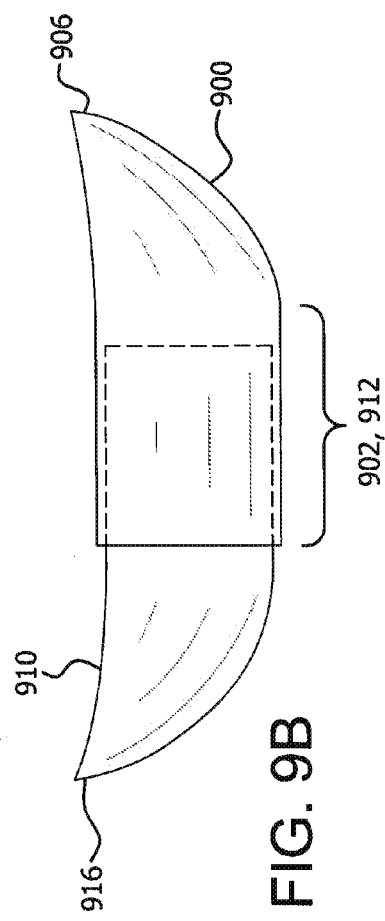
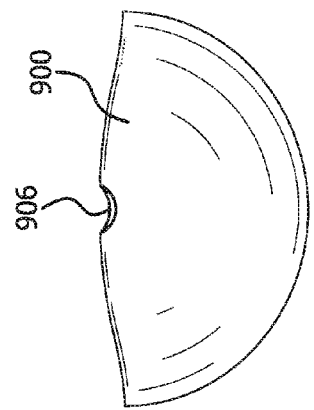
FIG. 9A
FIG. 9B
FIG. 9C

Figure 11A

Uncovered Balloon Data*

| Sample | Balloon Size (mm) | Rated Burst Pressure (ATM) | FRENCH SIZE vs. PULL THROUGH FORCE (Lb) | | | | | | | | | | | |
|---|---|---|---|---|---|---|---|---|---|---|---|---|---|---|
| | | | 22 F | 21 F | 20F | 19 F | 18 F | 17 F | 16 F | 15 F | 14 F | 13 F | 12 F | 11 F |
| 1 | 29x26 | 3.00 | | | | | 2.01 | 1.7 | 1.78 | 2.92 | 2.54 | 3.22 | 4.09 | 4.62 |
| 2 | 29x26 | 3.00 | | | | | 1.89 | 1.82 | 2.27 | 2.73 | 2.38 | 2.92 | 3.37 | 3.71 |
| 3 | 29x26 | 3.00 | | | | | 1.85 | 2.01 | 2.69 | 3.03 | 2.73 | 3.64 | 3.67 | 5.15 |
| 4 | 29x26 | 3.00 | | | | | 1.82 | 1.7 | 2.23 | 2.5 | 2.12 | 2.88 | 3.11 | 3.79 |
| 5 | 29x26 | 3.00 | | | | | 2.08 | 2.42 | 2.31 | 2.92 | 2.46 | 3.83 | 3.33 | 3.6 |
| 6 | 29x26 | 3.00 | | | | | 2.04 | 2.69 | 2.38 | 2.76 | 3.11 | 3.37 | 4.4 | 4.32 |
| 7 | 29x26 | 3.00 | | | | | 2.01 | 1.85 | 2.04 | 2.27 | 2.35 | 3.18 | 4.36 | 4.55 |
| 8 | 29x26 | 3.00 | | | | | 2.54 | 2.5 | 2.8 | 3.3 | 3.49 | 4.24 | 4.32 | 5.12 |
| 9 | 29x26 | 3.00 | | | | | 1.85 | 1.82 | 2.01 | 2.38 | 2.95 | 2.54 | 3.64 | 4.36 |
| 10 | 29x26 | 3.00 | | | | | 1.85 | 2.54 | 2.73 | 2.8 | 2.99 | 3.11 | 3.79 | 4.05 |
| AVERAGE: | | 3.00 | | | | | 1.99 | 2.11 | 2.32 | 2.76 | 2.71 | 3.29 | 3.81 | 4.33 |
| STD. DEV: | | 0.000 | | | | | 0.214 | 0.387 | 0.336 | 0.311 | 0.419 | 0.499 | 0.466 | 0.549 |

Note: The rated burst pressure was 3.00 ATM, the actual burst pressure averaged about 3.2 ATM
*per manufacturer testing

Figure 11B

Covered Balloon Data

| Sample | Balloon Size (mm) | Burst Pressure (ATM) | FRENCH SIZE vs. PULL THROUGH FORCE (Lb) | | | | | | | | | | | |
|---|---|---|---|---|---|---|---|---|---|---|---|---|---|---|
| | | | 22 F | 21 F | 20F | 19 F | 18 F | 17 F | 16 F | 15 F | 14 F | 13 F | 12 F | 11 F |
| 1 | 29x26 | | 6.12 | | | | 3.28 | 5.44 | 4.75 | 5.40 | 7.32 | 7.66 | 11.70 | |
| 2 | 29x26 | 9.68 | 5.51 | 3.74 | 4.20 | 3.71 | 4.91 | 5.21 | 6.25 | 6.57 | 9.31 | 11.50 | | N/A |
| 3 | 29x26 | 10.73 | 6.41 | 5.07 | 4.35 | 4.48 | 4.10 | 5.32 | 5.50 | 5.99 | 8.31 | 9.58 | | N/A |
| AVERAGE: | | 10.21 | 6.01 | 4.41 | 4.27 | 4.09 | 1.150 | 5.32 | 1.063 | 5.99 | 8.31 | 9.58 | 11.70 | N/A |
| STD. DEV: | | 0.742 | 0.459 | 0.943 | 0.110 | 0.547 | 1.150 | 0.161 | 1.063 | 0.824 | 1.406 | 2.714 | N/A | N/A |

HIGH STRENGTH BALLOON COVER

CROSS-REFERENCE TO RELATED APPLICATIONS

This application claims priority to provisional application Ser. No. 61/500,555 filed Jun. 23, 2011, incorporated herein in its entirety by reference.

FIELD OF THE INVENTION

This disclosure relates generally to a method of making a medical device, and more particularly to a method of fabricating a high burst strength, low profile medical balloon.

BACKGROUND OF THE INVENTION

Balloon angioplasty is a widely used procedure for expanding constricted body passageways, such as arteries and other blood vessels. In an angioplasty procedure, an uninflated angioplasty balloon attached to a catheter is delivered to a constricted region of a body passageway. Once the balloon is in position at the constricted region, fluid is injected through a lumen of the catheter and into the balloon. The balloon consequently inflates and exerts pressure against the constricted region to expand the passageway. After use, the balloon is collapsed, and the catheter is withdrawn.

Balloons have a number of critical design parameters. One is rated burst pressure, which is the statistically-determined maximum pressure to which a balloon may be inflated without rupturing. In order to expand hard, calcified lesions, it is desirable that the balloon have a rated burst pressure of at least 15 bar. It is also desirable that the balloon have a low wall thickness to minimize the profile of the delivery system. For a given balloon material, however, there is a trade-off between burst pressure and wall thickness, in that the burst pressure generally decreases when the wall thickness is reduced.

Accordingly, there is a need for a means of increasing the strength of a balloon to attain a higher rated burst pressure while maintaining a low delivery profile.

SUMMARY OF THE INVENTION

An embodiment comprises a catheter balloon having a working length and an expanded and an unexpanded diameter. At least partially surrounding the balloon is a balloon cover having a length and an expanded and unexpanded diameter. Wherein the balloon cover comprises first and second portions, wherein the first and second portions each comprise a working length integrally connected to a tapered end having an aperture located at an apex of the tapered end and the tapered ends of the first and second portions are located at opposite ends of the balloon cover, and the first and second working lengths of the first and second cover portions overlap for a substantial portion of the balloon working length.

Another embodiment comprises a balloon cover having a length, an unexpanded and expanded diameter, and first and second portions, wherein the first and second portions each comprise a working length integrally connected to a tapered end having an aperture located at an apex of the tapered end, and wherein the tapered ends of the first and second portions are located at opposite ends of the balloon cover, and the first and second working lengths substantially overlap.

Another embodiment comprises a balloon cover having a length, first and second portions, an unexpanded and expanded diameter, and an intermediate section comprising first and second ends, wherein the first and second portions each comprise a working length integrally connected to a tapered end having an aperture located at an apex of the tapered end, wherein the tapered ends of the first and second portions are located at opposite ends of the balloon cover and wherein the first end of the intermediate section overlaps with the working length of the first portion and the second end of the intermediate section overlaps with the working length of the second portion.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIGS. 1A and 1B are top plane views of a balloon catheter and balloon cover in accordance with an embodiment;

FIGS. 3B through 3E are partial cross-sectional and side views of balloon covers having different aperture locations relative to the balloon tapered portion, in accordance with embodiments;

FIGS. 6A through 6E are front, right, rear, left and top plane views of a mandrel and a film lay-up strap in accordance with an embodiment;

FIGS. 9A through 9C are top, front and right side plane views of a folded balloon cover in accordance with an embodiment;

FIGS. 11A and 11B are tabulations of burst and pull through test results for covered and uncovered balloons in accordance with embodiments;

DETAILED DESCRIPTION OF THE ILLUSTRATED EMBODIMENTS

Figure 2:
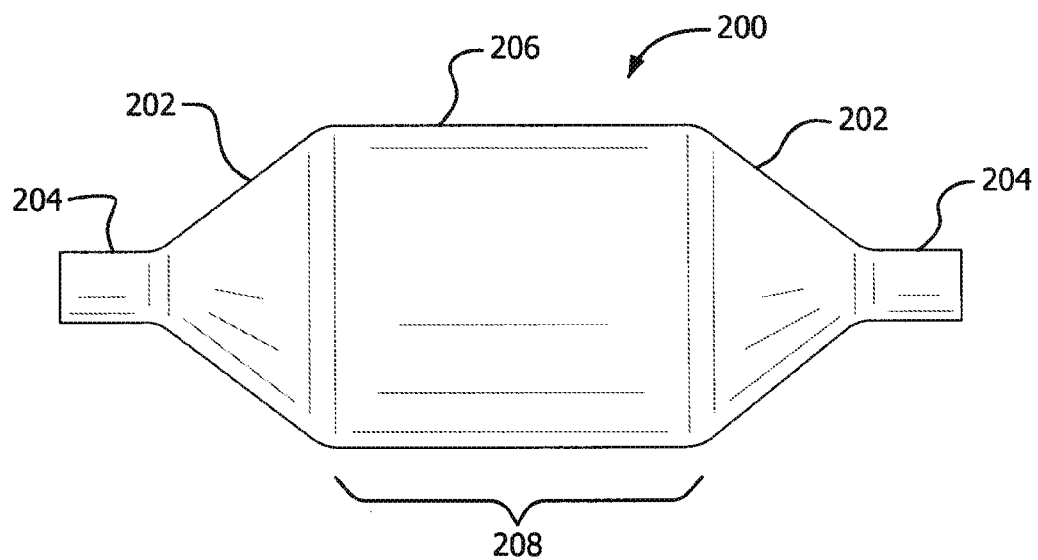
FIG. 2 is a schematic drawing of a typical medical balloon.

It will be apparent to those skilled in the art that various modifications and variations can be made in the present invention without departing from the spirit or scope of the invention. Thus, it is intended that the present invention cover the modifications and variations of the invention provided they come within the scope of the appended claims and their equivalents.

Described herein are embodiments of methods of making a reinforced medical balloon. The methods provide a high-strength, thin-walled medical balloon that can withstand high inflation pressures without rupturing. As used herein, the term "proximal" relates to a direction that is "closest to the heart", while "distal" relates to a direction that is "furthest from the heart".

FIG. 1A is a side view of a catheter system 100 having a balloon 106 and a balloon cover 108 in accordance with an embodiment. Shown is a distal hub 102, a catheter shaft 104 and a balloon 106 that is shown deflated. The balloon cover 108 is shown surrounding a substantial portion of the balloon 106. FIG. 1B is a side view of a balloon catheter system 100 having a hub 102, a catheter shaft 104 and a balloon 106 that is shown inflated. The balloon cover 108 is shown surrounding a substantial portion of the balloon 106. Also shown is a cross-sectional plane defined as "3-3".

FIG. 2 is a side view of a typical medical balloon 200. Shown is a balloon 200 having two opposed leg portions 204 that are integrally connected to shoulder/tapered portions 202. For the purposes of this disclosure, "working length" is defined as the length of the straight body section 206 of a balloon 200, which comprises the approximate length between the opposed shoulder/tapered portions 202. The leg portions 204, shoulder/tapered portions 202 and the working length 208 define a balloon overall length.

Figure 3A:
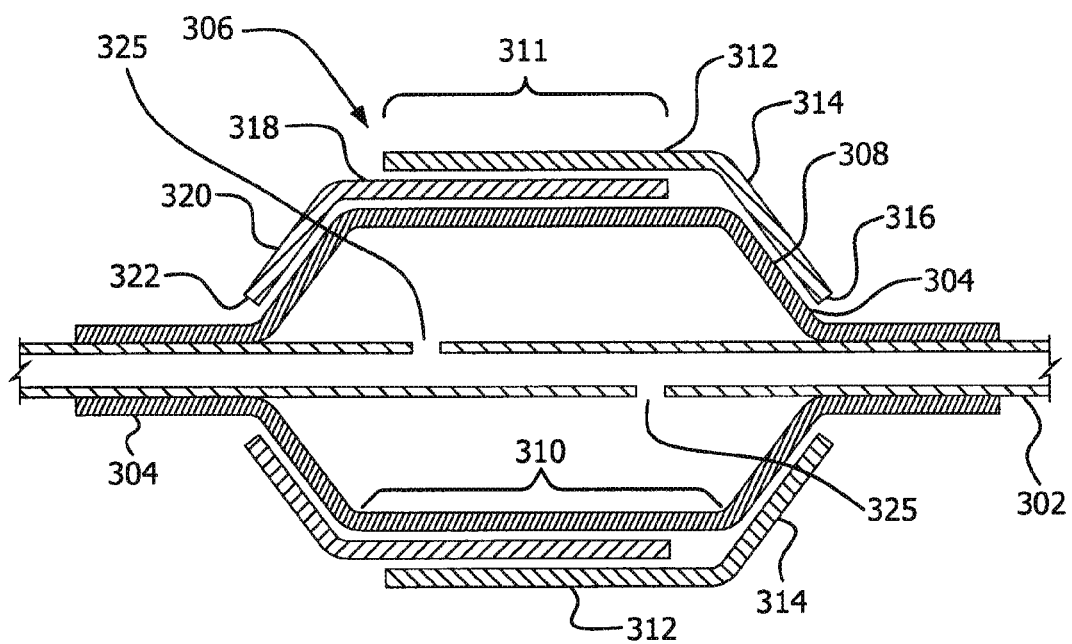
FIG. 3A is a cross-sectional view of a catheter shaft, a balloon and a balloon cover in accordance with an embodiment.

FIG. 3A is a side-view cross-section taken along cross-sectional plane 3-3 of FIG. 1B, showing the various portions of a balloon 304 and balloon cover 312 in accordance with an embodiment. Shown is a catheter shaft 302, inflation ports 325, and the balloon 304 coupled to the catheter shaft 302. The balloon cover 306 is positioned around balloon shoulder/tapered portions 308 and a working length 310 of the balloon 304. The balloon cover 306 comprises a first outer portion 312 that has a working length 311 approximating the balloon working length 310. The working length 311 of the first outer portion 312 of the balloon cover 306 is integrally connected to a tapered end 314 having an aperture 316 located at an apex of the tapered end 316. The balloon cover 306 further comprises a second inner portion 318 that has a working length 311 approximating the balloon working length 310. The working length 311 of the second inner portion 318 of the balloon cover 306 is integrally connected to a tapered end 320 having an aperture 322 located at an apex of the tapered end 320.

The balloon cover 306 therefore has tapered ends (314, 320) of first outer and second inner portions (312, 318) that are located at opposite ends of the balloon cover 306. In addition, the working lengths 311 of the first outer and second inner portions (312, 318) overlap for a substantial portion of a balloon working length 310. For the purposes of this disclosure, "substantial portion of the balloon working length" means about over 50% to about 100% of the balloon working length 310. In specific embodiments, "substantial portion of the balloon working length" comprises over and/or about 60%, about 70%, about 80%, about 90%, about 95%, about 98% of the balloon working length 310.

Shown in FIG. 3B is a partial cross-sectional side view of a first outer portion 312 of a balloon cover 306, shown overlaying an inflated balloon 304. The additional layers shown in FIG. 3A have been omitted for clarity. The aperture 316 is shown positioned about 20% "up along" the tapered shoulder portion 308 of the balloon 304. As indicated, a position that is "zero %" up the tapered shoulder portion 308 is located at the junction of the balloon leg 321 and the balloon tapered shoulder 308. A position that is "100% up the taper" is located at the junction of the balloon tapered shoulder 308 and the balloon working length 310, shown in FIG. 3A. FIG. 3C is an end view of a complete (non-cross-sectioned) balloon with a surrounding first cover portion 312. Shown is a cover aperture 316 positioned about 20% up the tapered shoulder portion 308 of the balloon 304. Also shown are inflated balloon diameter 324, balloon leg diameter 326 and first cover portion aperture diameter 328a. The position of the cover aperture 316 relative to the tapered shoulder portion 308 of the balloon 304 can be expressed as a ratio of cover aperture diameter 328a to the inflated balloon diameter 324. Similarly, the position of the cover aperture 3316 relative to the tapered shoulder portion 308 of the balloon 304 can be expressed as a ratio of cover aperture diameter 328a to the balloon leg diameter 326.

FIGS. 3D and 3E are similar to previous FIGS. 3B and 3C. As shown in FIG. 3D, the cover aperture 316 is shown positioned about 75% "up along" the tapered shoulder portion 308 of the balloon 304. FIG. 3E is an end view of a complete (non-cross-sectioned) balloon 304 with a surrounding first cover portion 312. Shown is a cover aperture 316 positioned about 75% up the tapered shoulder portion 308 of the balloon 304. Also shown are inflated balloon diameter 324, balloon leg diameter 326 and first cover portion aperture diameter 328b. The position of the cover aperture 328b relative to the tapered shoulder portion 308 of the balloon 304 can be expressed as a ratio of cover aperture diameter 328b to the inflated balloon diameter 324. Similarly, the position of the cover aperture 328b relative to the tapered shoulder portion 308 of the balloon 304 can be expressed as a ratio of cover aperture diameter 328b to the balloon leg diameter 326. Note that FIGS. 3C and E are not drawn to scale, but are intended to illustrate a difference in the size of the cover aperture 304.

The large cover aperture sizes are useful for many applications including for designing a balloon fail safe so that the balloon will fail only in the uncovered area such as the tapered shoulder portion 308 of the balloon 304 and/or for reducing pull through forces (see below) by reducing the amount of material in the tapered shoulder portion 308 and thus reducing profile in that area.

Endoluminal balloons are typically blow molded from a uniform wall thickness tube. Once molded the tube is stretched and has varying wall thickness. The balloon is commonly thickest at the leg portions and becomes thinner up the tapered shoulder portion to the straight body section, which is the thinnest.

Thickness is inverse to the stress on the balloon while under pressure. The thinnest wall of the blow molded balloon is under the greatest stress. The thick wall at the leg portions of the balloon introduces un-needed strength and extra mass. These thick leg portions reduce the minimum introducer size through which a balloon can be withdrawn.

Thus, embodiment presented herein comprise a cover which provides additional strength to the balloon wall. In particular, the thinnest part of the balloon is the strongest part of the cover and vice versa. Balloon covers provided herein increase the rated burst pressure of a balloon with minimal addition to the withdrawal profile.

Balloons and balloon covers can be fabricated from a variety of commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX).

Balloon covers of embodiments provided herein can be fabricated by a variety of methods such as molding, vacuum/pressure forming, film-wrapping, film-layering, fiber winding or other methods known in the art.

Figure 4:
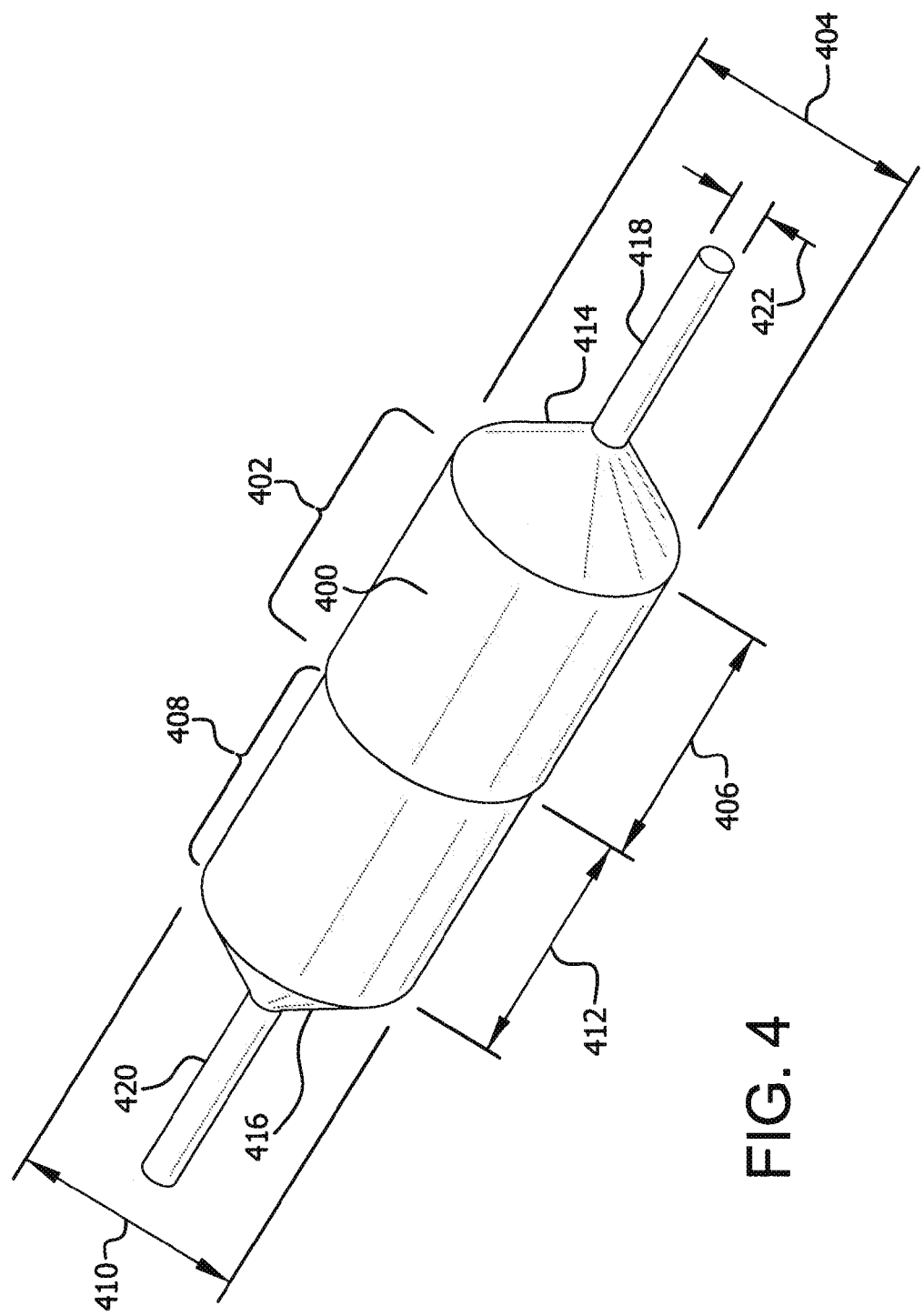
FIG. 4 is a perspective view of a mandrel used to form balloon cover portions in accordance with an embodiment.

The following describes one embodiment of a method, utilizing thin, polymeric film lay-ups that can be used to fabricate various balloon covers according to the present invention. This method can comprise the following steps:

1) A stepped metallic, film lay-up mandrel can be fabricated according to FIG. 4. Shown is a metallic mandrel 400 having a first cylindrical portion 402. The first cylindrical portion 402 has a diameter 404 and a length 406. Similarly, the metallic mandrel 400 has a second cylindrical portion 408. The second cylindrical portion 408 has a diameter 410 and a length 412. The first and second cylindrical portions 402, 408 are integrally connected to opposing tapered shoulder portions (414, 416). The opposing tapered shoulder portions (414, 416) are integrally connected to opposing shafts (418, 420) having diameters 422. The lengths (406, 412), diameters (404, 410) and shoulder (414, 416) dimensions can be tailored to accommodate the dimensions of a subsequent underlying balloon. Lengths (406, 412) can range from about 1 mm to more than 100 mm, diameters (404, 410) can range from about 1 mm to more than 100 mm and shoulder angles can range from about 10° to about 90°. In one embodiment, the cover diameter is undersized by about at least 5% relative to the balloon diameter. Undersizing the balloon cover by at least 5% allows the balloon cover to bear the radial load, thus not allowing the balloon to fail, at least in the covered region of the balloon.

The mandrel 400 can be used to form two cover cup portions having overlapping working lengths. For the working lengths to overlap, a first cup is fabricated to have a working length inner diameter that is slightly larger than the working length outer diameter of the second cup. The difference between the working length diameters is dictated by the different diameters of the first cylindrical portion 402 and the second cylindrical portion 408. For example diameter 404 can be about 0.012" larger than diameter 410, accommodating covers with a 0.006" wall thickness.

Figure 5:
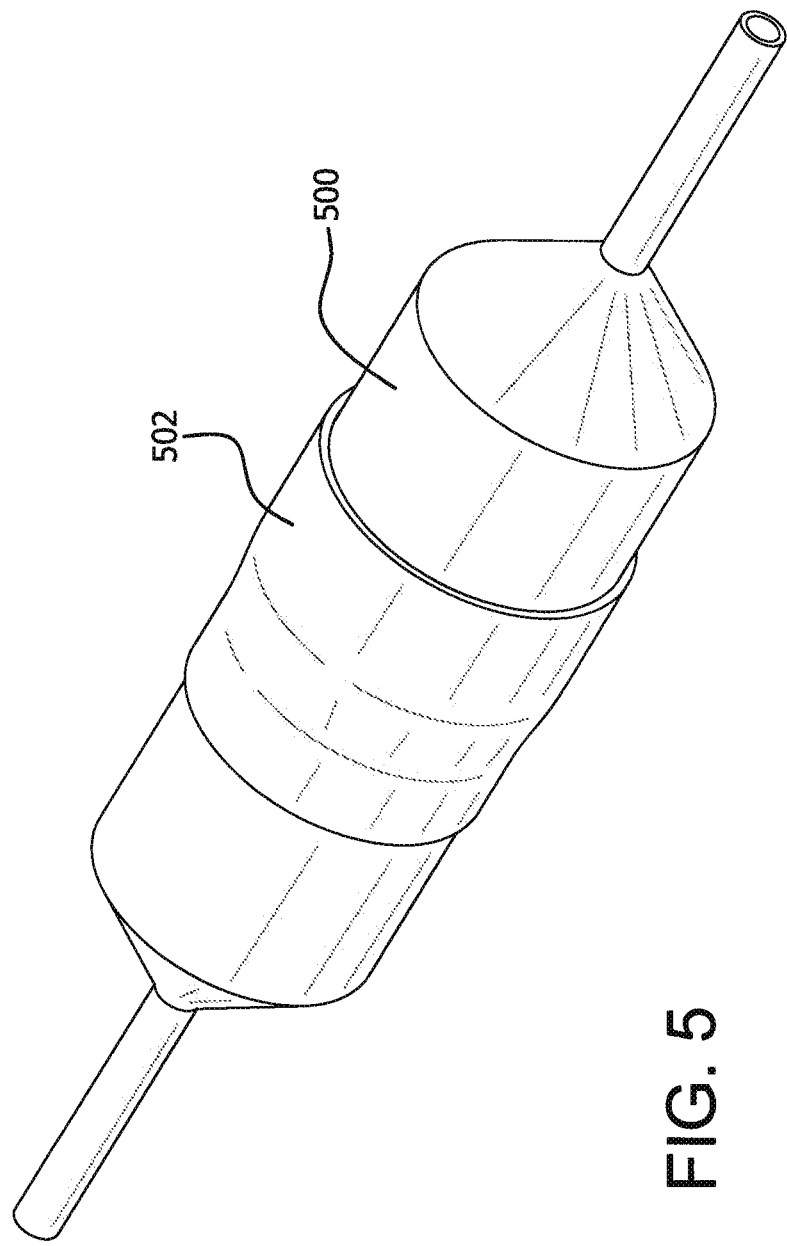
FIG. 5 is a perspective view of a mandrel used to form balloon cover portions, in accordance with an embodiment, further showing a manufacturing aid.

2) One of the shafts (418, 420) can be mounted onto a rotatable collet to hold the mandrel and allow rotation of the mandrel during subsequent processing steps. As shown in FIG. 5, a manufacturing aid, in the form of a film 502 coated with a thermoplastic adhesive, can be added to the center portion of the mandrel 500. For example, two to five circumferential wraps can be applied. The layers can be secured by reflowing the thermoplastic adhesive by the application of heat, such as by a soldering iron or other heating means. The width of the film and the location on the mandrel, can be selected to accommodate the dimensions of desired cover portions. A suitable film can comprise expanded polytetrafluoroethylene (ePTFE) imbibed or coated with a thermoplastic fluoroelastomer or other combinations of polymeric films and thermoplastics.

Figure 6D:
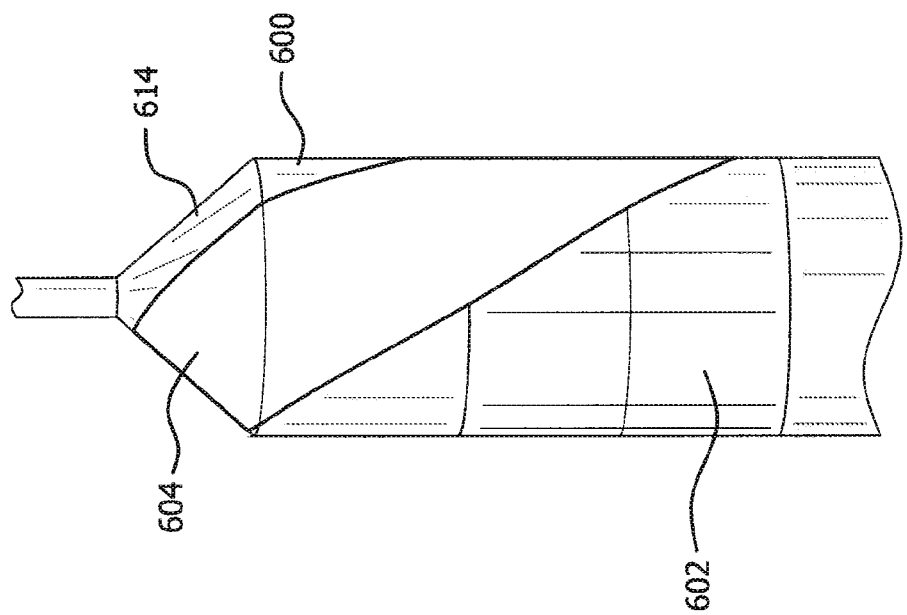
Figure 6C:
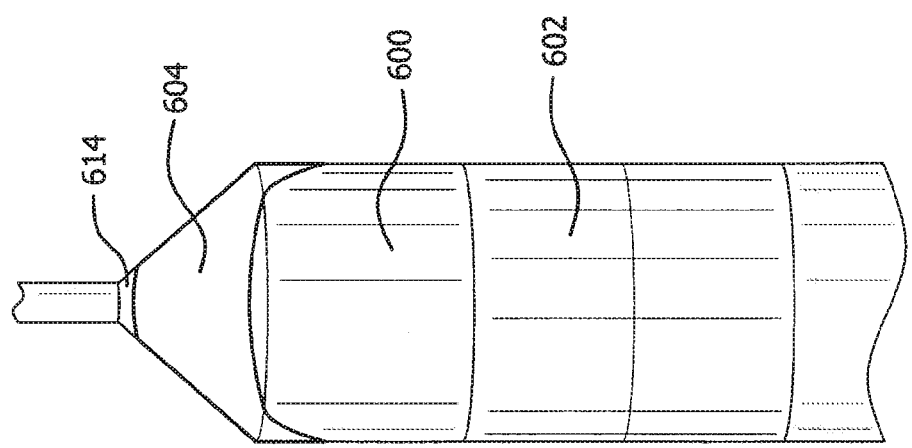

3) As described in FIGS. 6A through 6E, a series of film layers or straps can be applied onto the first cylindrical portion (larger diameter relative to the second cylindrical portion) and onto the integrally connected tapered shoulder portion of the mandrel. Shown in FIG. 6A is a front plane view of a mandrel 600 with a strap of a thin polymeric film 604 positioned over a tapered shoulder portion 614. Shown in FIG. 6B is a right side plane view (of FIG. 6A) of a mandrel 600 with a strap of a thin polymeric film 604 positioned over a tapered shoulder portion 614. As shown, the film strap 604 is closely abutted against the base of the integral shaft 618. Similarly, FIG. 6C is a rear side plane view (of FIG. 6A) of a mandrel 600 with a strap of a thin polymeric film 604 positioned over a tapered shoulder portion 614. FIG. 6D is a left side plane view (of FIG. 6A) of a mandrel 600 with a strap of a thin polymeric film 604 positioned over a tapered shoulder portion 614. Note that the width and size of the straps can vary depending on the application.

4) The portions of the film strap 604 overlying the film/thermoplastic manufacturing aid 602 can be smoothed out and heat tacked to the manufacturing aid 602, resulting in one film strap formed onto the mandrel 600.

Figure 6E:
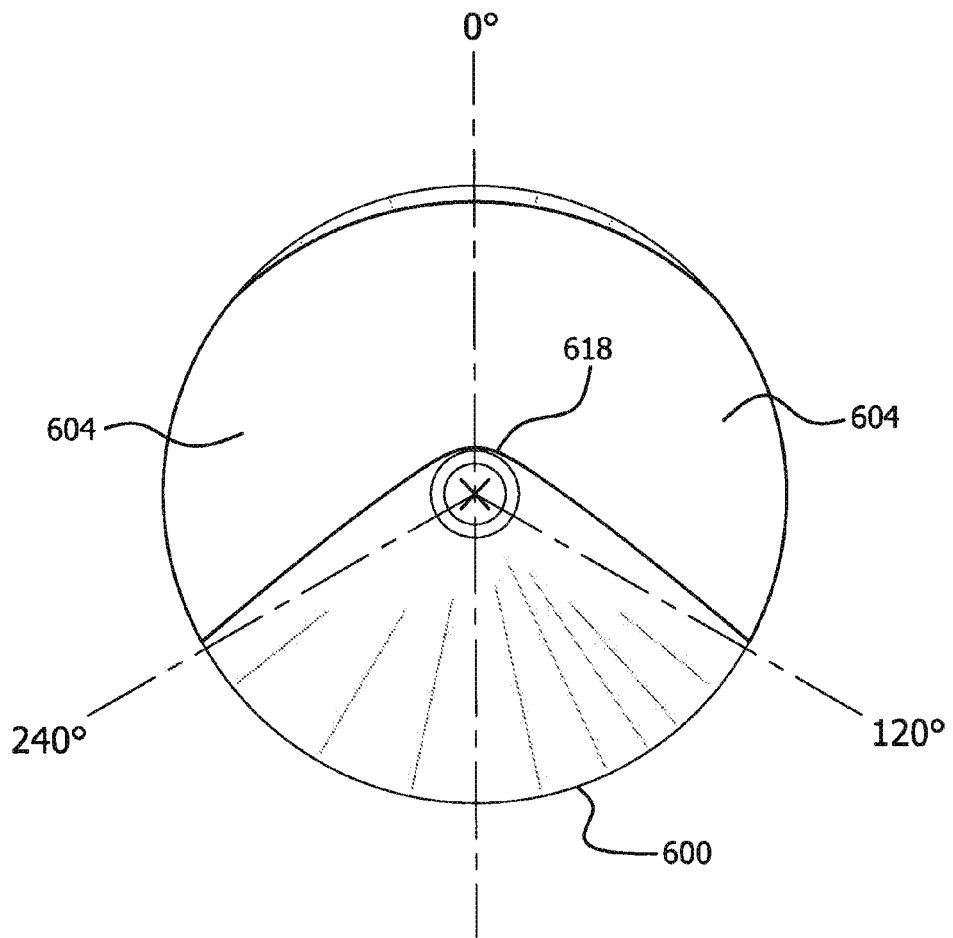

5) FIG. 6E is a top plane view (of FIG. 6A) showing the film 604 closely abutted against the integral shaft 618. For reference, the film shown is oriented (relative to the mandrel 600) at a "zero degree" position. Two additional film straps can be added in a "clocked" fashion whereby the point where the film strap abuts the integral shaft 618 is oriented about 120° relative to the previous film strap. The two additional film straps can be heat tacked to the manufacturing aid 602, resulting in three film straps formed onto the mandrel 600.

6) The polymeric film used as a film strap can comprise an expanded polytetrafluoroethylene (ePTFE) film, coated on one side with a thermoplastic (or thermoset) adhesive. The three film straps of FIGS. 6A through 6E can have the adhesive side oriented out and away from the mandrel.

ePTFE may be made as taught by U.S. Pat. Nos. 3,953,566 and 4,187,390, both of which are incorporated by reference herein. In another embodiment, the ePTFE is impregnated with a thermoplastic (or thermoset) adhesive, silicone adhesive, silicone elastomer, silicone dispersion, polyurethane or another suitable elastomeric material. Impregnation involves at least partially filling the pores of the porous ePTFE. U.S. Pat. No. 5,519,172 teaches in detail the impregnation of porous ePTFE with elastomers, such as the one taught in U.S. Pat. No. 7,462,675. In one embodiment, the film comprises an elastomer so that when formed into a balloon cover in accordance with the present invention, the cover will expand and contract, thus also contracting and/or refolding the balloon.

Figure 7A:
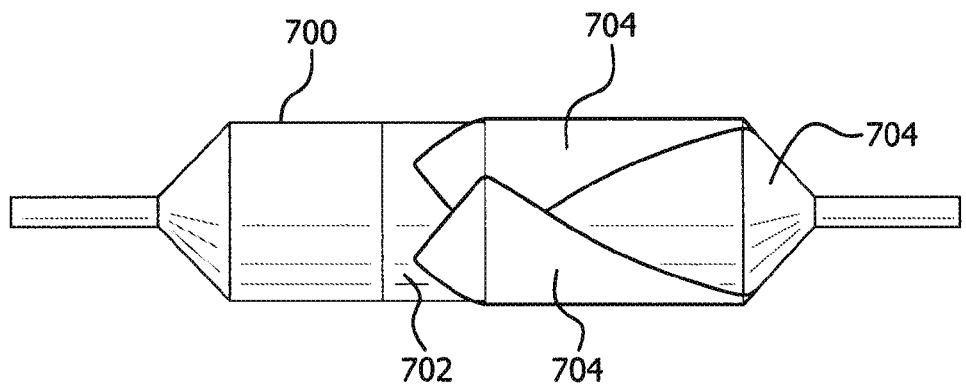
FIGS. 7A and 7B are top plane views of a mandrel with film lay-up straps and an additional radial film layer in accordance with an embodiment.
Figure 7B:
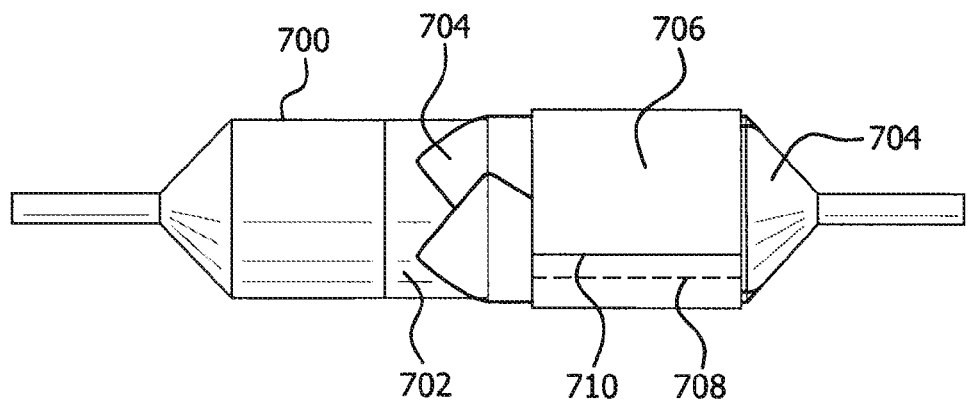

7) A circumferentially wrapped film layer can be added to the wrapped mandrel from step 5). Shown in FIG. 7A is a mandrel 700 having a wrapped film manufacturing aid 702 and three polymeric film straps 704 wrapped according to step 5). As shown in FIG. 7B, a film layer 706 can be circumferentially wrapped about the first cylindrical portion (FIG. 4, 402). The circumferentially wrapped film layer 706 can have an end-to-end (708, 710) overlap as shown. The polymeric film used as a circumferential wrap 706 can comprise an ePTFE film, coated on one side with a thermoplastic (or thermoset) adhesive. The circumferential wrap 706 can have the adhesive side oriented out and away from the mandrel. The overlapping ends of the film can be heat tacked and bonded together.

8) Three additional film straps can be added to the first cylindrical portion (FIG. 4, 402) according to the method of step 5). The first additional film strap can be added in "clocked" fashion whereby the point where the film strap abuts the integral shaft 618 (FIG. 6) is oriented about 60° relative to the previous film strap. The second and third additional film straps can then be added in a "clocked" fashion whereby the point where the film strap abuts the integral shaft 618 (FIG. 6) is oriented about 120° relative to the previous film strap.

9) The portions of the film straps overlying the film/thermoplastic manufacturing aid 602 (FIG. 6) can be smoothed out and heat tacked to the manufacturing aid.

10) The polymeric film used as a film strap can comprise an ePTFE film, coated on one side with a thermoplastic (or thermoset) adhesive. The three additional film straps of step 8) can have the adhesive side oriented inward and towards the mandrel.

11) A circumferentially wrapped film layer can be added to the wrapped mandrel from step 8), similar to that of step 7). The polymeric film used as a circumferential wrap can comprise an ePTFE film, coated on one side with a thermoplastic (or thermoset) adhesive. The circumferential wrap can have the adhesive side oriented inward and towards the mandrel.

12) Using a process as similar to that described in FIGS. 6A through 6E, a series of film layers or straps can be applied onto the second cylindrical portion (smaller diameter relative to the first cylindrical portion) and onto the integrally connected tapered shoulder portion of the mandrel.

13) Six film straps can be applied according to the process of steps 3-6, 8-9). The adhesive side of the film straps can be oriented out and away from the mandrel.

14) Two layers of a circumferentially wrapped film can be added to the wrapped mandrel from step 13). The circumferentially wrapped film can be applied according to the process of step 7) and can have the adhesive side of the film straps oriented out and away from the mandrel.

15) The mandrel with film wrapped first and second cylindrical portions and integrally connected tapered shoulder portions can then be heat treated in an air convection (e.g. in an over set of 250° C. for about 30 minutes). The heat treatment reflows the thermoplastic adhesive and bonds the various film layers together. The mandrel and films can then be ambient, forced air cooled for about 30 minutes.

Figure 8:
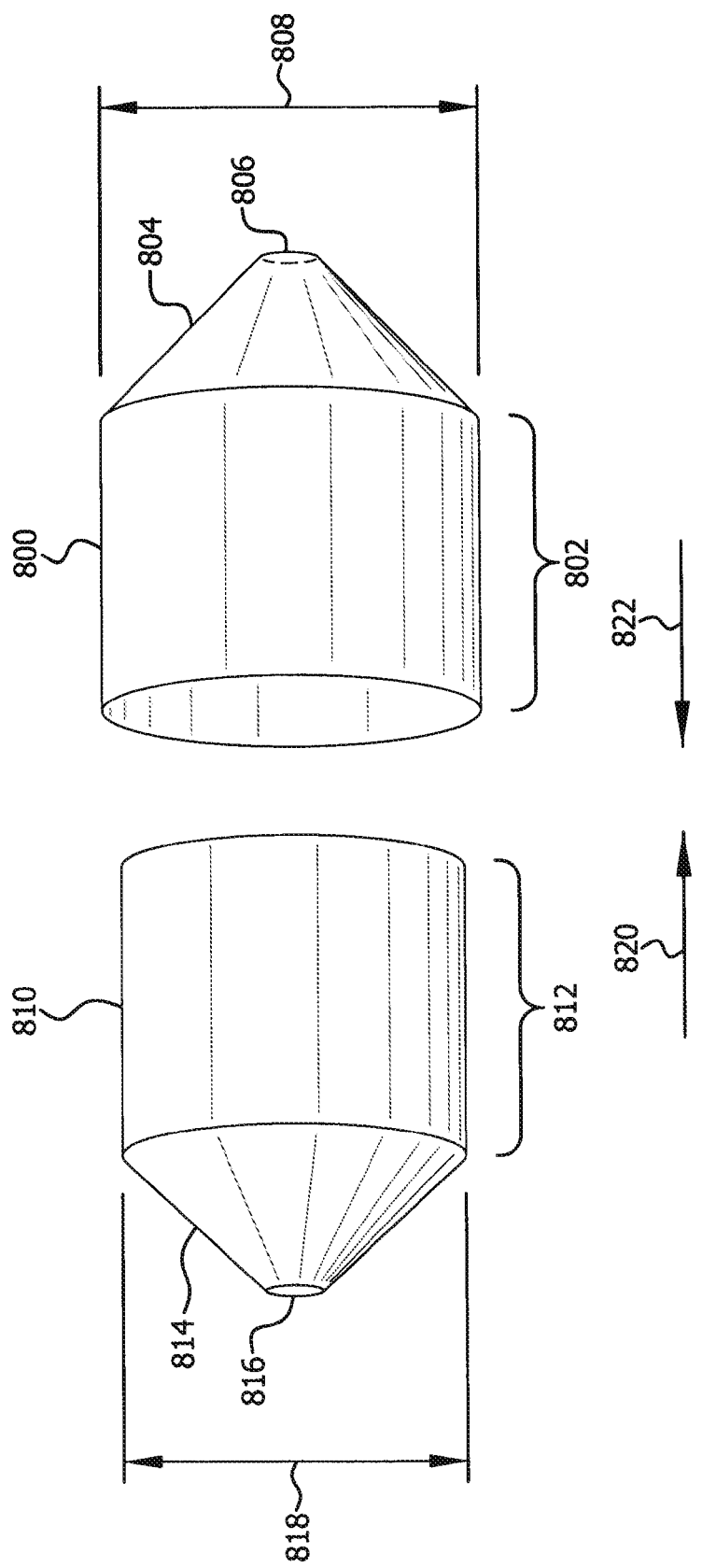
FIG. 8 is a perspective view of first and second balloon cover portions in accordance with an embodiment.

16) The bonded films on the first and second cylindrical portions and integrally connected tapered shoulder portions can then be circumferentially cut and removed from the mandrel. The location of the circumferential cut can determine the desired working lengths of the first and second cylindrical cup portions. Shown in FIG. 8 is a first, large diameter outer balloon cover portion 800 having a working length 802 integrally connected to a tapered end or shoulder portion 804. The tapered end or shoulder portion 804 has an aperture 806 located at an apex of the tapered end 804. Also shown in FIG. 8 is a second, small diameter outer balloon cover portion 810 having a working length 812 integrally connected to a tapered end or shoulder portion 814. The tapered end or shoulder portion 814 has an aperture 816 located at an apex of the tapered end 814.

17) As further shown in FIG. 8, the second, small diameter outer balloon cover portion 810 can be inserted into the first, large diameter outer balloon cover portion 800 by translating the second and first cylindrical cup portions as indicated by direction arrows (820, 822), so that the working lengths (812, 802) are substantially overlapped. For the purposes of this embodiment "substantially overlapped" means that about over 50% to about 100% of the working lengths (812, 802) of the first and second cylindrical cup portions, which correspond to the cover working lengths 311 shown in FIG. 3A, overlap. In specific embodiments, "substantially overlapped" comprises about 60%, about 70%, about 80%, about 90%, about 95%, about 98% of the cover working length.

18) In preparation for bonding the working lengths (802, 812) together, the first and second cover portions (800, 810) are flattened-out to form a cup-shaped assembly as generally depicted in FIGS. 9A through 9C. FIG. 9A is a top plane view of flattened first 900 and second 910 cover portions. As shown, the working lengths (902, 912) are substantially overlapped. Also shown are apertures (906, 916) located at the apexes of the tapered ends of the first balloon and second balloon cover portions. FIG. 9B is a front plane view of the cup-shaped assembly shown in FIG. 9A, while FIG. 9C is a right side plane view of the cup-shaped assembly shown in FIG. 9A.

Figure 10A:
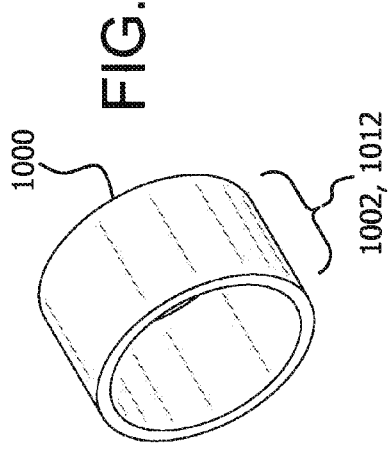
FIGS. 10A through 10C are perspective, front and right plane views of a folded balloon cover, depicting a bonding process in accordance with an embodiment.
Figure 10C:
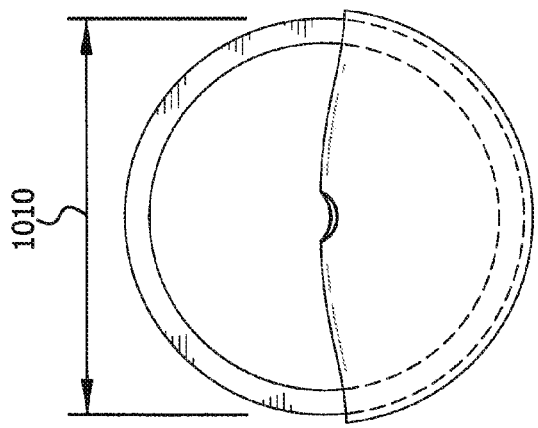
Figure 10B:
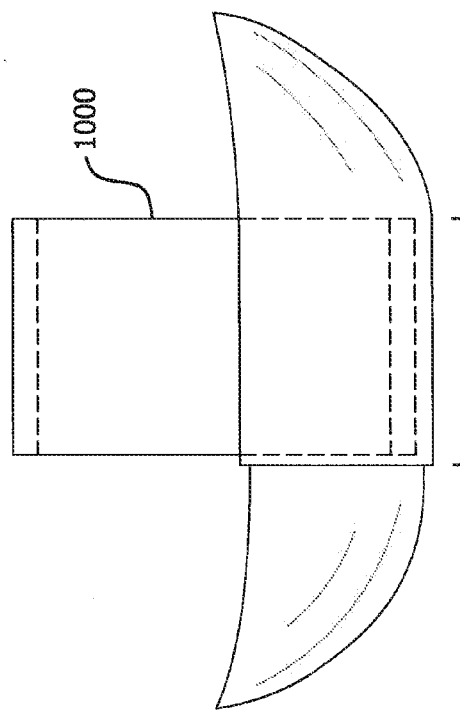

19) FIGS. 10A through 10C describe a process used to bond the first and second cover portion working lengths together. Shown in FIG. 10A is a metallic ring 1000 having a length (1002, 1012) that approximates the first and second cover portion working lengths (1002, 1012). As shown in FIGS. 10B and 10C, the ring 1000 can be inserted into the cup-shaped assembly of FIGS. 9A through 9C. As shown in FIG. 10C, the ring 1000 has a diameter 1010 dimensioned to mate into the cup-shaped assembly of FIGS. 9A through 9C. A layer of high temperature polymeric film, such as Kapton® can then be wrapped around the ring and cup-shaped assembly. A high temperature fiber can be wrapped about the high temperature polymeric film, the ring and cup-shaped assembly. When heated, the high temperature fiber can shrink and contract about the high temperature polymeric film and the ring and cup-shaped assembly, and therefore apply pressure onto the overlapped working lengths of the balloon cover portions. After securing the high temperature fiber, the components can be heated in an air convection oven to about 250° C. for about 30 minutes. The pressure applied by the contracting high temperature fiber causes the thermoplastic layers within the overlapped working lengths to reflow and form a bond between the layers.

20) The components from step 20) can then be ambient forced air cooled for about 30 minutes. The high temperature fiber, high temperature film and the metallic ring can be removed and the two bonded balloon cover portions can be expanded. A compacted balloon, mounted onto a catheter, can be inserted into the expanded balloon cover portions, thereby forming a covered balloon as previously described in FIG. 3. The balloon can be inflated to conform to the balloon cover and then be partially deflated. While the balloon is partially deflated, an adhesive can be injected into the balloon cover apertures (906, 916 of FIG. 9A) to bond the opposing ends of the balloon cover to the underlying balloon. The adhesive can be cured, forming a catheter system having a proximal balloon and a balloon cover according to the present invention, as depicted in FIGS. 1A and 1B. In one embodiment, the balloon cover does not cover the leg portions 204, as shown in FIG. 2, of a balloon. In another embodiment, the balloon cover is not attached to a catheter, or any other structure that a balloon is mounted. In another embodiment, the balloon cover does not have leg portions (in accordance with FIG. 2).

Various alternative embodiments of the balloon cover can be fabricated. For example, balloon covers in accordance with an embodiment can incorporate additional balloon cover portions so that a balloon cover has more than two portions. A balloon cover in accordance with an embodiment can have two, three, four, five, six, seven, eight, nine, ten or more overlapping portions referred to as working lengths. Embodiments of balloon covers can also be formed to have tapered length portions and/or non-circular cross-sectional profiles. Balloon covers in accordance with an embodiment can also incorporate strengthening elements such as high strength fibers, braids or other elements to enhance the balloon cover strength or rigidity. Balloon covers in accordance with embodiments can also incorporate surface treatments to provide drugs, therapeutic agents, lubricious coatings or radiopaque markings. A guidewire channel can also be provided between a balloon and a balloon cover resulting in an optional "rapid exchange" configuration.

The balloon cover in accordance with embodiments presented herein is scalable to different size balloons. Thus, a 24 mm to 37 mm balloon with the cover of the invention may have a burst pressure of 9 Atm to 20 Atm. Similarly smaller diameter balloons, e.g. a 5 mm diameter balloon can be converted to a high pressure balloon by the addition of the balloon cover in accordance with embodiments presented herein. In one embodiment, an about 29 mm balloon with a rated burst pressure of 3 Atm is converted to a high pressure balloon with a burst pressure of about 11 Atm with the addition of the balloon cover in accordance with an embodiment. In another embodiment, a 5 mm diameter balloon has a burst pressure of about 45 Atm with the addition of the balloon cover in accordance with an embodiment.

Thus one embodiment comprises a catheter balloon comprising an inflatable medical balloon having a balloon working length and an expanded and unexpanded diameter, and a balloon cover having a length and an expanded and unexpanded diameter, wherein the balloon cover comprises first and second portions, wherein the first and second portions each comprise a working length integrally connected to a tapered end having an aperture located at an apex of the tapered end, and wherein the tapered ends of the first and second portions are located at opposite ends of the balloon cover and the first and second working lengths of the first and second cover portions overlap for a substantial portion of the balloon working length. In another embodiment, the medical balloon is a non-compliant balloon. In another embodiment, the medical balloon is a compliant balloon. In another embodiment, the balloon cover comprises a fibrillated material. In another embodiment, the fibrillated material is ePTFE. In another embodiment, fibrils in the ePTFE are oriented in a radial direction. In another embodiment, wherein the balloon cover is made from straps of ePTFE that are adhered to each other. In another embodiment, the straps are laid in multiple angular orientations on the working length and the tapered ends of the balloon cover. In another embodiment, the balloon cover is adhered to the medical balloon. In another embodiment, working lengths that overlap for a substantial portion of the balloon working length also cover a portion of a balloon shoulder. In another embodiment, the expanded diameter of the balloon cover is smaller than the expanded diameter of the medical balloon.

Another embodiment comprises a balloon cover comprising a length, an unexpanded and expanded diameter, and first and second portions, wherein the first and second portions each comprise a working length integrally connected to a tapered end having an aperture located at an apex of the tapered end, and wherein the tapered ends of the first and second portions are located at opposite ends of the balloon cover and the first and second working lengths overlap for a substantial portion of the length of the balloon cover.

Figure 12A:
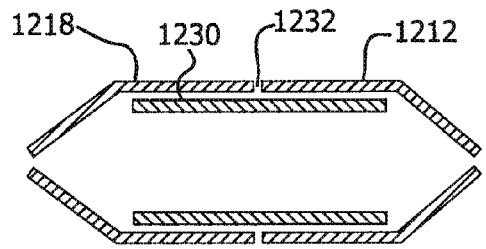
FIGS. 12A through 12E are cross-sectional side views of balloon covers in accordance with embodiments incorporating an additional intermediate cover portion.
Figure 12B:
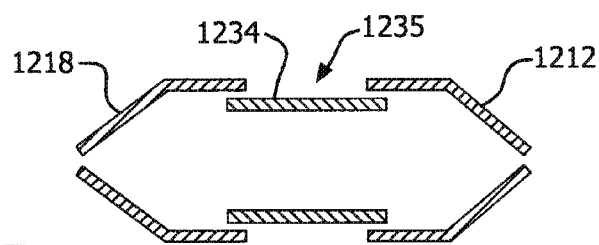

In another embodiment, FIGS. 12A through 12E show partial cross-sectional side views of first and second balloon cover portions (1212, 1218) along with various intermediate cover portions (1230, 1234, 1236, 1238, 1240). Shown in FIG. 12A are first and second balloon cover portions (1212, 1218) and an intermediate cover portion 1230. The first and second balloon cover portions (1212, 1218) are shown closely abutted defining a small gap 1232. FIG. 12B is similar to previous FIG. 12A, showing first and second balloon cover portions (1212, 1218) and an intermediate cover portion 1234. The first and second balloon cover portions (1212, 1218) are shown spaced apart with a gap 1235, with the intermediate cover portion 1234 bridging the gap 1235, and overlapped by a portion of the first and second balloon cover portions (1212, 1218).

Figure 12C:
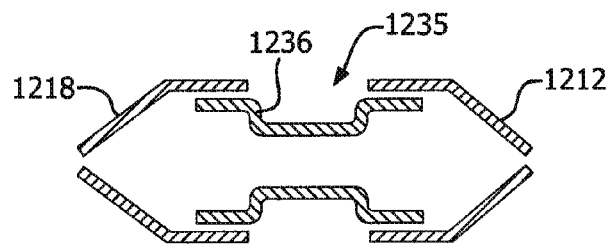

FIG. 12C shows first and second balloon cover portions (1212, 1218) and an intermediate cover portion 1236 having a stepped diameter that is smaller than the diameters of the first and second balloon cover portions. The first and second balloon cover portions (1212, 1218) are shown spaced apart with a gap 1235, with the intermediate cover portion 1234 bridging the gap 1235, and overlapped by a portion of the first and second balloon cover portions (1212, 1218).

Figure 12D:
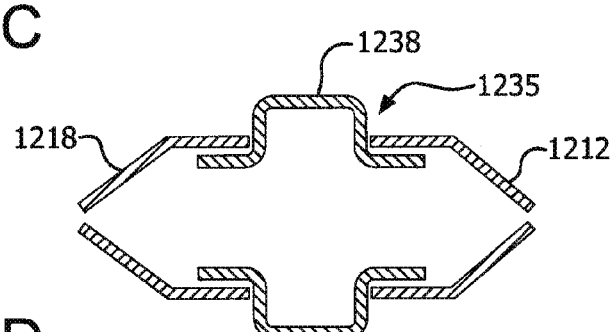

FIG. 12D shows first and second balloon cover portions (1212, 1218) and an intermediate cover portion 1238 having a stepped diameter that is larger than the diameters of the first and second balloon cover portions. The first and second balloon cover portions (1212, 1218) are shown spaced apart with a gap 1235, with the intermediate cover portion 1236 bridging the gap 1235, and overlapped by a portion of the first and second balloon cover portions (1212, 1218).

Figure 12E:
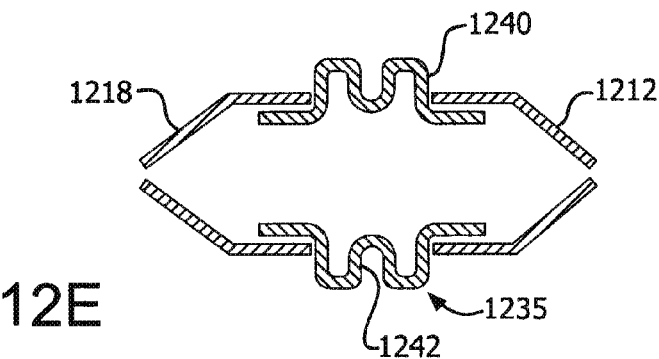

FIG. 12E shows first and second balloon cover portions (1212, 1218) and an intermediate cover portion 1240 having a stepped diameter that is larger than the diameters of the first and second balloon cover portions. The larger stepped diameter 1240 incorporates a groove 1242 along the circumference of the stepped diameter. The first and second balloon cover portions (1212, 1218) are shown spaced apart with a gap 1235, with the intermediate cover portion 1240 bridging the gap 1235, and overlapped by a portion of the first and second balloon cover portions (1212, 1218).

Balloon covers of embodiments provided herein can incorporate one, two, three, four, five or more additional intermediate cover portions. The intermediate cover portions can have similar or dissimilar shapes or profiles and can be configured for a specific application. For example, a stepped intermediate cover portion can be configured to expand and anchor a heart valve stent.

Thus, in another embodiment, a balloon cover comprises a length, first and second portions, an unexpanded and expanded diameter, and an intermediate section comprising first and second ends, wherein the first and second portions each comprises a working length integrally connected to a tapered end having an aperture located at an apex of the tapered end, wherein the tapered ends of the first and second portions are located at opposite ends of the balloon cover and wherein the first end of the intermediate section overlaps with the working length of the first portion and the second end of the intermediate section overlaps with the working length of the second portion.

Another embodiment, a balloon cover comprises a length, first and second portions, an unexpanded and expanded diameter, and an intermediate section comprising first and second ends, wherein the first and second portions each comprises a working length integrally connected to a tapered end having an aperture located at an apex of the tapered end, wherein the tapered ends of the first and second portions are located at opposite ends of the balloon cover and wherein the first end of the intermediate section overlaps with the working length of the first portion and the second end of the intermediate section overlaps with the working length of the second portion. In another embodiment, when the balloon cover is in its expanded diameter, the intermediate section confers to the balloon cover a shape selected from the group consisting of an hourglass, triangular, square, rectangular, oval or other polygon. In another embodiment, the intermediate section is made from a different material than the first and second portions. In another embodiment, the intermediate section is made from ePTFE.

Figure 13:
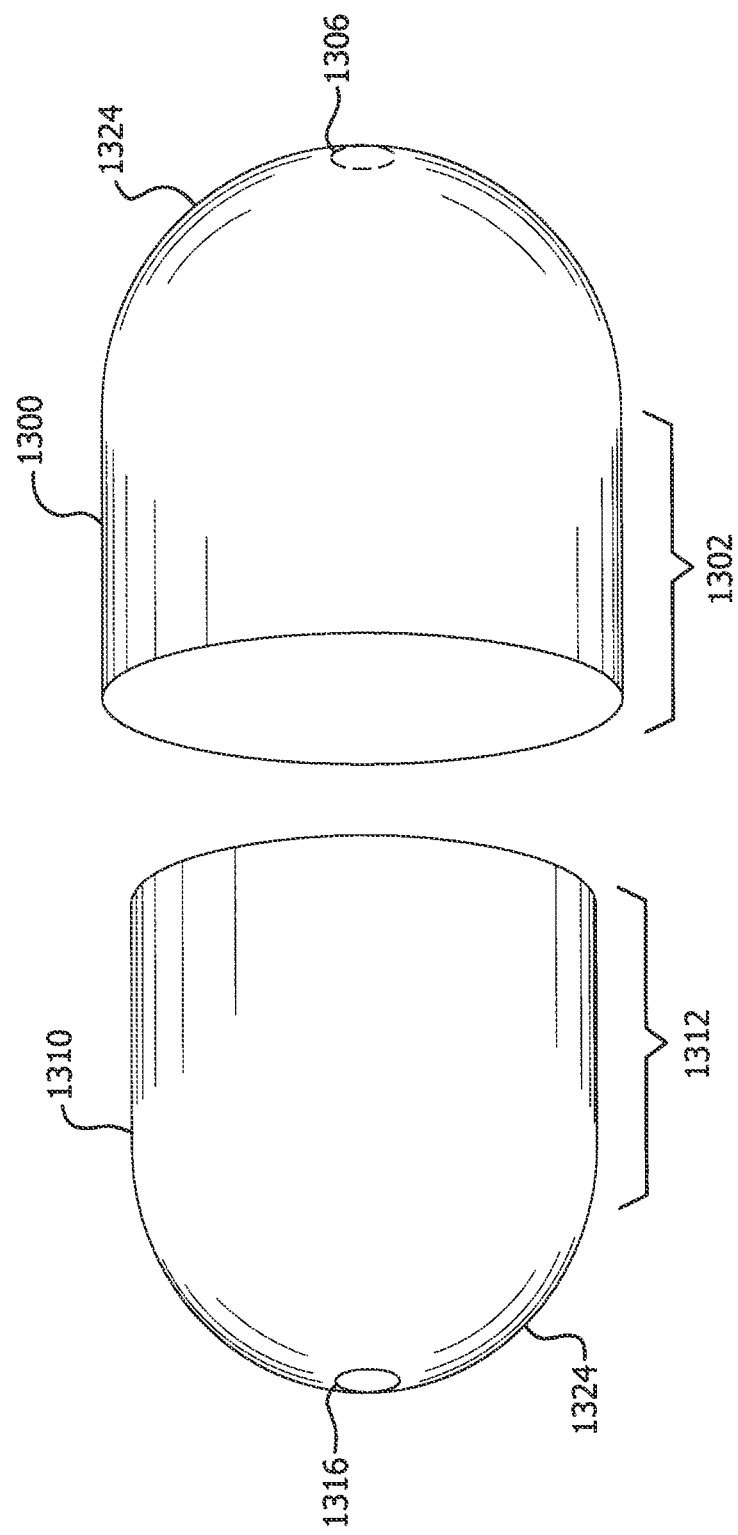
FIG. 13 is a perspective view of first and second balloon cover portions in accordance with an embodiment having essentially spherical tapered portions.

In another embodiment as shown in FIG. 13 is similar to the embodiment of FIG. 8. Shown in FIG. 13 are first and second balloon cover portions (1300, 1310) having working lengths (1302, 1312), opposing apertures (1306, 1316) and essentially spherical tapered shoulder portions 1324. The tapered shoulder portions 1324 can be configured to match the inflated profile of a specific balloon.

EXAMPLES

Without intending to limit the scope of the invention, the following examples illustrate how various embodiments of the invention may be made and/or used Example 1

A balloon cover of the present invention was fabricated according to the previously described steps 1) through 20), with the following additional details:

In step 1), the mandrel had the following dimensions: first cylindrical portion diameter was 1.142", first cylindrical portion length was 1.378", second cylindrical portion diameter was 1.130", second cylindrical portion length was 1.378", the opposing tapered shoulders had 90° included angles and the opposing shafts had diameters of 0.157". The mandrel was fabricated from 300 series stainless steel.

In step 2), the manufacturing aid (film) was about 0.75 wide and about 8" long. The film strap comprised a densified fluoropolymer as described in U.S. Pat. No. 7,521,010 to Kennedy et al., laminated with a fluoroelastomer thermoplastic adhesive, as described in U.S. Pat. No. 7,462,675 to Chang et al. The film had the following properties:

Composite thickness=5 μm
Composite mass per area=11.1 g/m2
Machine Direction Matrix Tensile Strength=356 MPa.

Three full circumferential wraps were layered onto the mandrel. The heat-tacking soldering iron was set to about 650° F.

In steps 3) through 15) the film straps were about 0.75" wide and were of the same film as the manufacturing aid described above. The circumferential wrapped film was about 1" wide and was of the same film as the manufacturing aid described above.

In step 15) the heat treat temperature was about 250° C. and the heat treatment time was about 30 minutes.

In step 16), the first and second cylindrical cup portions were cut to have working lengths of about 25 mm.

In step 19) the metallic ring had a length of about 24 mm, an outer diameter of about 38 mm, an inner diameter of about 35 mm and was fabricated from 300 series stainless steel. The high temperature polymeric film was 0.004" thick, 40 mm wide Kapton®. The high temperature fiber was a heat shrinkable fluoropolymer. The heat treat temperature was about 250° C. and the heat treatment time was about 30 minutes.

In step 20), the balloon was fabricated from Polyethylene Terephthalate (PET, Thermoplastic Polyester) and had a nominal outer diameter of about 29 mm, a nominal working length of about 26 mm, a nominal wall thickness (along the working length) of about 0.0028", included cone angles of about 90° and opposing leg outer diameters of about 3.4 mm. The balloon cover was bonded to the underlying balloon with LockTite® adhesive part number 495 and was then ambient cured.

The balloon cover was undersized (relative to the balloon inflated diameter) by about 5%, allowing the balloon cover to absorb the load imparted to the cover by the inflated balloon.

Example 2

The balloon with attached balloon covers from EXAMPLE 1 was subjected to a pull through test. The pull through test was designed to measure the force required to pull a deflated balloon through a series of gage holes. The test was designed to emulate the force required to retract a deflated balloon back into an introducer sheath.

A vertical universal mechanical testing system (Instron®, Model 5564, Norwood, Mass., USA) with a 10.2 kg tension load cell was configured to measure pull through forces. A water bath was aligned to the testing system and heated to about 37° C. A longitudinally split gage, having a series of varying diameter pull through holes was fixed within the heated water bath.

A balloon catheter with balloon covers (from EXAMPLE 1) was provided. A distal portion of the balloon catheter shaft was clamped to the load cell head. The gage with a series of varying diameter pull through holes was "split open" to allow a proximal portion of the catheter shaft to be inserted into a first, large diameter hole (22 F or about 0.29" with a chamfered/broken edge lead in). The gage halves were then aligned and clamped together, surrounding the proximal portion of the catheter shaft. The balloon was then inflated to about 2 ATM and then deflated with a vacuum. The vacuum was maintained with a stopcock located on the proximal end of the catheter. The deflated balloon was then pulled up through the gage hole at rate of about 10"/minute while the instant pull force was recorded.

The gage was then split open and the catheter shaft was positioned into the next smaller gage hole. The gage was reassembled, the balloon was re-inflated to about 2 ATM and deflated as previously described. The catheter/balloon was then pulled through the gage hole while the instant pull force was recorded.

The test sequence was repeated using progressively smaller gage pull through holes. The test sequence was terminated if the balloon ruptured/leaked during inflation, or if the pull through force exceeded a pre-determined limit. The pull through hole diameters, for a typical 29 mm underlying balloon with balloon covers according to EXAMPLE 1, ranged from 22 F (about 0.29") to 11 F (about 0.145").

Underlying PET balloons, without the covers of the present invention were also evaluated on the pull through test to generate comparative data.

Example 3

The balloon with attached balloon covers from EXAMPLE 1 was subjected to a balloon compliance, inflation/burst test.

The balloon compliance, inflation/burst test was designed to measure the balloon diameter vs. internal pressure along with determining the internal balloon pressure required to rupture/burst the balloon and attached covers from EXAMPLE 1.

A balloon compliance/burst test system was provided (Interface Associates, Laguna Niguel, Calif., USA, Model PT3070). The test system had a water bath heated to about 37° C., a pressurized water feed/pressure measurement system and a laser micrometer to measure the outer diameter of the expanded balloon and balloon covers. The balloon compliance/burst test parameters are displayed in TABLE 1 below:

TABLE 1

| Test Parameter | Setting |
|---|---|
| Pressurization Ramp Rate (ml/s) | 1.0 |
| Pressurization Alarm Drop Pressurization Time* (sec) | 2.50 |
| Pressurization Max Pressure (ATM) | 50.00 |
| Pressurization Max Volume (ml) | 200.00 |
| Pressurization Max Diameter (mm) | 55.00 |
| Start Up Position | 0.10 |
| Start Up Vacuum Pressure | −0.50 |
| Pressure Units | ATM |
| Diameter Units | mm |
| Ramp Target Offset Pressure (ATM) | 0.00 |
| Pre-Fill Volume (ml) | 20.00 |
| Pre-Fill Pressure (ATM) | 1.00 |
| Pre-Fill Rate (ml/s) | 0.50 |

The balloon with attached balloon covers was purged of air by a series of vacuum air withdrawals followed by water inflations. The purging was repeated until no more air could be withdrawn from the balloon catheter. After air purging, the catheter was subjected to the compliance/burst test.

Underlying PET balloons, without the covers of the present invention were also evaluated on the compliance/burst test to generate comparative data.

Example 4

Balloons with attached covers from EXAMPLE 1 were subjected to the pull through test (EXAMPLE 2) and to the balloon compliance, inflation/burst test (EXAMPLE 3). Additionally, underlying or uncovered balloons were subjected to the pull through and compliance/burst test to generate comparative data. The test results are displayed in FIGS. 11A and 11B.

These data show that the presence of a balloon cover presenting accordance with embodiments presented herein significantly raises the burst strength of the covered balloon without significantly compromising the pull through force.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present invention is further directed to embodiments having different combinations of the features described above and claimed below. As such, the invention is also directed to other embodiments having any other possible combination of the dependent features claimed below.

What is claimed is:

1. A catheter balloon comprising:
an inflatable medical balloon having a balloon working length and an expanded and unexpanded diameter; and
a balloon cover having a length and an expanded and unexpanded diameter;
wherein the balloon cover includes first and second portions, wherein the first and second portions each comprise a working length integrally connected to a tapered end having an aperture located at an apex of the tapered end, each aperture extending circumferentially around the medical balloon and wherein the first and second portions are not adhered to the inflatable medical balloon;
wherein the tapered end of the first portion and the tapered end of the second portion are each located at opposite ends of the balloon cover relative to the each other;
wherein the working lengths of the first and second portions of the balloon cover overlap at least a substantial portion of the balloon working length, and at least a portion of the working lengths of the first and second portions overlap each other; and
wherein the tapered ends of the first and second portions do not overlap the working lengths of the first and second portions such that the balloon cover is thinner at the tapered ends of the first and second portions than along the portion of the balloon cover that corresponds to the portion of the working lengths of the first and second portions that overlap each other along at least a portion of the balloon working length.

2. The catheter balloon of claim 1, wherein the medical balloon is a non-compliant balloon.

3. The catheter balloon of claim 1, wherein the medical balloon is a compliant balloon.

4. The catheter balloon of claim 1, wherein the balloon cover comprises a fibrillated material.

5. The catheter balloon of claim 4, wherein the fibrillated material is ePTFE.

6. The catheter balloon of claim 5, wherein the balloon cover is made from straps of ePTFE that are adhered to each other.

7. The catheter balloon of claim 6, wherein the straps are in multiple angular orientations with respect to each other on the working length and the tapered ends of the balloon cover.

8. The catheter balloon of claim 1, wherein the balloon cover first and second portions cover a portion of a balloon shoulder.

9. A balloon cover for an inflatable medical balloon comprising:
a first and second portions portion, wherein the first and second portions each comprise a working length integrally connected to a tapered end having an aperture located at an apex of the tapered end, each aperture extending circumferentially around the inflatable medical balloon the balloon cover, wherein the first and second portions are not adhered to the inflatable medical balloon, and wherein the tapered end of the first portion and the tapered end of the second portion are each located at opposite ends of the balloon cover relative to each other, and the working lengths of the first and second portions overlap at least a substantial portion of a working length of the inflatable medical balloon and at least a portion of the working lengths of the first and second portions overlap each other, wherein the tapered ends of the first and second portions do not overlap the working lengths of the first and second portions such that the balloon cover is thinner at the tapered ends of the first and second portions than along the portion of the balloon cover that corresponds to the portion of the working lengths of the first and second portions that overlap each other along at least a portion of the balloon working length.

10. The balloon cover for an inflatable medical balloon of claim 9, wherein the medical balloon is a non-compliant balloon.

11. The balloon cover for an inflatable medical balloon of claim 9, wherein the medical balloon is a compliant balloon.

12. The balloon cover for an inflatable medical balloon of claim 9, wherein the balloon cover comprises a fibrillated material.

13. The balloon cover for an inflatable medical balloon of claim 12, wherein the fibrillated material is ePTFE.

14. The balloon cover for an inflatable medical balloon of claim 13, wherein the balloon cover is made from straps of ePTFE that are adhered to each other.

15. The catheter balloon cover for an inflatable medical balloon of claim 14, wherein the straps are in multiple angular orientations with respect to each other on the working length and the tapered ends of the balloon cover.

16. The balloon cover for an inflatable medical balloon of claim 9, wherein the balloon cover first and second portions cover a portion of a balloon shoulder.

* * * * *